(12) United States Patent
Alifano et al.

(10) Patent No.: US 8,529,900 B2
(45) Date of Patent: Sep. 10, 2013

(54) METHODS FOR THE TREATMENT, THE PROGNOSTIC ASSESSMENT AND THE STAGING OF NON-SMALL CELL LUNG CANCER

(75) Inventors: Marco Alifano, Paris (FR); Patricia Forgez, Paris (FR)

(73) Assignees: INSERM (Institut National de la Sante et de la Recherche Medicale), Paris (FR); Assistance Publique Hopitaux de Paris, Paris (FR)

( * ) Notice: Subject to any disclaimer, the term of this patent is extended or adjusted under 35 U.S.C. 154(b) by 254 days.

(21) Appl. No.: 12/934,191

(22) PCT Filed: Apr. 14, 2009

(86) PCT No.: PCT/EP2009/054395
§ 371 (c)(1),
(2), (4) Date: Oct. 28, 2010

(87) PCT Pub. No.: WO2009/127619
PCT Pub. Date: Oct. 22, 2009

(65) Prior Publication Data
US 2011/0044906 A1    Feb. 24, 2011

(30) Foreign Application Priority Data

Apr. 16, 2008   (EP) .................... 08300180

(51) Int. Cl.
| | | |
|---|---|---|
| *A61K 31/00* | (2006.01) | |
| *A61K 38/00* | (2006.01) | |
| *A61K 39/00* | (2006.01) | |
| *A61K 39/395* | (2006.01) | |
| *A61K 49/00* | (2006.01) | |
| *A61B 5/055* | (2006.01) | |
| *A01N 61/00* | (2006.01) | |

(52) U.S. Cl.
USPC ......... 424/138.1; 424/9.1; 424/9.2; 424/9.34; 424/130.1; 424/178.1; 514/1; 514/1.1; 514/19.2; 514/19.3

(58) Field of Classification Search
None
See application file for complete search history.

(56) References Cited

U.S. PATENT DOCUMENTS

2006/0276527 A1 * 12/2006 Tidmarsh ................ 514/406
2007/0020178 A1    1/2007 Weichert et al.
2008/0050378 A1 *  2/2008 Nakamura et al. ......... 424/138.1

FOREIGN PATENT DOCUMENTS

WO      2005/090603      9/2005

OTHER PUBLICATIONS

Takahashi et al. The neuromedin u-growth hormone secretagogue receptor 1b/neurotensin receptor 1 oncogenic signaling pathway as a therapeuitc target for lung cancer. Cancer Research 66 (19): 9408-9419, published online Oct. 3, 2006.*
International Search Report in PCT/EP09/54395, dated Jul. 6, 2009.
Takahashi et al., Cancer Res., 66(19):9408-9419 (2006), XP002449360.
Evers, Peptides, 27(10):2424-2433 (2006), XP002484676.

* cited by examiner

*Primary Examiner* — Alana Harris Dent
(74) *Attorney, Agent, or Firm* — McAndrewsm Held & Malloy Ltd.

(57) ABSTRACT

The present invention relates to methods for the treatment, the prognosis and the diagnosis of non-small cell lung cancer.

2 Claims, 8 Drawing Sheets

SEQUENCE LISTING

```
<160> NUMBER OF SEQ ID NOS: 11

<210> SEQ ID NO 1
<211> LENGTH: 21
<212> TYPE: DNA
<213> ORGANISM: Artificial
<220> FEATURE:
<223> OTHER INFORMATION: synthetic siRNA

<400> SEQUENCE: 1
aagaagttca tcagcgccat c                                            21

<210> SEQ ID NO 2
<211> LENGTH: 19
<212> TYPE: DNA
<213> ORGANISM: Artificial
<220> FEATURE:
<223> OTHER INFORMATION: synthetic siRNA

<400> SEQUENCE: 2
gcaatgttga caatatacc                                               19

<210> SEQ ID NO 3
<211> LENGTH: 15
<212> TYPE: DNA
<213> ORGANISM: Artificial
<220> FEATURE:
<223> OTHER INFORMATION: synthetic primer

<400> SEQUENCE: 3
gctgacgtag aagag                                                   15

<210> SEQ ID NO 4
<211> LENGTH: 20
<212> TYPE: DNA
<213> ORGANISM: Artificial
```

```
<220> FEATURE:
<223> OTHER INFORMATION: synthetic primer

<400> SEQUENCE: 4
cgtggagctg tacaacttca                                                 20

<210> SEQ ID NO 5
<211> LENGTH: 20
<212> TYPE: DNA
<213> ORGANISM: Artificial
<220> FEATURE:
<223> OTHER INFORMATION: synthetic primer

<400> SEQUENCE: 5
cagccagcag accacaaagg                                                 20

<210> SEQ ID NO 6
<211> LENGTH: 20
<212> TYPE: DNA
<213> ORGANISM: Artificial
<220> FEATURE:
<223> OTHER INFORMATION: synthetic primer

<400> SEQUENCE: 6
cagctcctgg agtctgtgct                                                 20

<210> SEQ ID NO 7
<211> LENGTH: 24
<212> TYPE: DNA
<213> ORGANISM: Artificial
<220> FEATURE:
<223> OTHER INFORMATION: synthetic primer

<400> SEQUENCE: 7
gttgaaaagc cctgctgtga caga                                            24

<210> SEQ ID NO 8
<211> LENGTH: 21
<212> TYPE: DNA
<213> ORGANISM: Artificial
<220> FEATURE:
<223> OTHER INFORMATION: synthetic primer

<400> SEQUENCE: 8
ttcaaatgag attgtggaaa a                                               21

<210> SEQ ID NO 9
<211> LENGTH: 21
<212> TYPE: DNA
<213> ORGANISM: Artificial
<220> FEATURE:
<223> OTHER INFORMATION: synthetic primer

<400> SEQUENCE: 9
agatcatctc tgcctgagta t                                               21

<210> SEQ ID NO 10
<211> LENGTH: 21
<212> TYPE: DNA
<213> ORGANISM: Artificial
<220> FEATURE:
<223> OTHER INFORMATION: synthetic primer

<400> SEQUENCE: 10
cggagtcaac ggatttggtc g                                               21
```

```
<210> SEQ ID NO 11
<211> LENGTH: 21
<212> TYPE: DNA
<213> ORGANISM: Artificial
<220> FEATURE:
<223> OTHER INFORMATION: synthetic primer

<400> SEQUENCE: 11
ttcaccacca tggagaaggc t                                              21
```

METHODS FOR THE TREATMENT, THE PROGNOSTIC ASSESSMENT AND THE STAGING OF NON-SMALL CELL LUNG CANCER

The present application is filed pursuant to 35 U.S.C. 371 as a U.S. National Phase application of International Patent Application No. PCT/EP09/54395, which was filed Apr. 14, 2009, claiming the benefit of priority to European Patent Application No. 08300180.0, which was filed on Apr. 16, 2008. The entire text of the aforementioned applications is incorporated herein by reference in its entirety.

FIELD OF THE INVENTION

The present invention relates to methods for the treatment, the prognostic assessment and the staging of non-small cell lung cancer.

BACKGROUND OF THE INVENTION

Neuropeptide-receptors complex are often deregulated during the neoplastic process. Several concomitant and well described oncogenic pathways are engaged by these complexes, caused by abnormal autocrine or paracrine regulation, and resulting in the enhancement of cancer progression (Heasley L E. Oncogene 20(13):1563-9, 2001). Amongst these complexes involved in cancer progression is the 13 amino acid Neurotensin (NTS) and its cognate high affinity neurotensin receptor 1 (NTRS1). NTS, which is mainly localized in the gastrointestinal tract, participates in local physiological functions by modulating the release of major substances, such as pancreatic and biliary secretions, substance P, prostaglandin, and others. NTSR1 expression is found in human tumors deriving mainly from epithelial origin, such as the colon, pancreas, prostate, and breast (Evers B M. Peptides 27(10):2424-33 2006; Souaze F et al, Cancer Res 66(12):6243-9 2006).

NTSR1 expression is minimally present or absent in normal epithelial cells. However, it is induced in the early stages of carcinogenesis by the activation of the Wnt/beta catenin pathway (Elek J et al. Anticancer Res 20(1A):53-8, 2000; Souaze F et al. Carcinogenesis 27(4):708-16, 2006). The activation of NTSR1 leads to cell proliferation, survival, mobility and invasiveness in specific cancer cell types via signalization through PKC, ERK1/2, RhoGTPases, NFkappa-B, or focal adhesion kinase (FAK) activation (Leyton J et al, Eur J Pharmacol; 442(3):179-86, 2002; Ehlers R A et al Biochem Biophys Res Commun 269(3):704-8, 2000; Zhao D et al, Mol Pharmacol 67(6):2025-31, 2005). The NTS-NTSR1 complex was shown to be involved in tumor growth by disrupting the neurotensinergic pathway, via a specific antagonist, in experimental tumors generated in nude mice from colon, breast and small cell lung cancer cells, and thereby causing a strong reduction in tumor growth (Souaze F et al. Cancer Res 66(12):6243-9 2006, Moody T W et al Peptides 22(1):109-15, 2001; Maoret J J et al. Int J Cancer 80(3):448-54, 1999.

Non-small cell lung cancer is the leading cause of cancer-related deaths. The size of the primary tumor, the invasion of loco-regional nodes and, the presence of distant metastases, determine the survival rate. These parameters are used to define the stage of the disease and to decide the optimal patient management.

In spite of the progress in medical and surgical treatments, long term survival remains poor, with overall values ranging from 10 to 20% at 5 years. Chemotherapy has overall, a limited impact on survival either when used as an adjuvant treatment after surgery, or as a primary treatment in metastatic subjects. At present, the impact of molecular targeted drugs on the outcome of patients with lung cancer is also limited (Heasley L E. Oncogene 20(13):1563-9, 2001).

Operable patients have an overall 5-year survival rate around 40% and among them, those with stage I disease experience figures of only 60-70%. Identifying patients with pathologic initial stages but with a high risk of recurrence would be extremely useful, in order to individually tailor further management, in terms of more strict follow-up and/or adjuvant treatments (Scott W J et al, Chest. 2003 January; 123(1 Suppl):188S-201S).

Therefore, objects of the present invention are to provide methods for the treatment, the prognostic assessment and the staging of non-small cell lung cancer.

SUMMARY OF THE INVENTION

The present invention describes that neurotensin receptor 1 (NTSR1) is expressed in non-small cell lung cancer cells, and that the activation of NTSR1 leads to cell proliferation, survival, mobility and invasiveness in non-small cell lung cancer cells. The present invention also describes that NTSR1 expression can be used as a marker to discriminate between non-small cell lung cancer tumors aggressiveness.

There is provided a method for treating non-small cell lung cancer, comprising the step of administering an effective amount of an inhibitor of the neurotensin activation of the neurotensin receptor 1 (NTSR1) to a subject in need thereof.

The present invention also provides a method for treating non-small cell lung cancer, comprising the step of administering an effective amount of a cytotoxic agent which binds to the neurotensin receptor 1 to a subject in need thereof.

The present invention also relates to a method of determining the prognosis of a subject suffering from non-small cell lung cancer, comprising the step of detecting the expression of NTRS1 in non-small cell lung cancer cells obtained from said subject, wherein the presence of expression of NTSR1 indicates that the subject has a poor prognosis.

The present invention also provides a method of detecting and localizing non-small cell lung cancer cells and their metastases in the body of a subject, to which a quantity sufficient for imaging of a labelled agent which binds to NTSR1 has been previously administered, comprising the step of subjecting said body to imaging.

DETAILED DESCRIPTION OF THE INVENTION

The present invention provides a method for treating non-small cell lung cancer, comprising the step of administering an effective amount of an inhibitor of the neurotensin activation of the neurotensin receptor 1 (NTSR1) to a subject in need thereof.

Also provided is an inhibitor of the neurotensin activation of the neurotensin receptor 1 (NTSR1) for the treatment of non-small cell lung cancer.

The expression "inhibitors of the neurotensin activation of NTSR1" should be understood broadly, this expression refers to agents down-regulating the expression of neurotensin or of neurotensin receptor 1, compounds that bind to neurotensin (NTS) or NTSR1 and inhibit the neurotensin activation of NTSR1, or a protease that can degrade NTS.

Examples of inhibitors of the neurotensin activation of NTSR1 may be selected from the group consisting of an agent down-regulating the expression of neurotensin or of neurotensin receptor 1, an antibody against neurotensin or a fragment thereof which binds to neurotensin, an antibody against the neurotensin receptor 1 or a fragment thereof which binds to the neurotensin receptor 1, an antagonist of the neurotensin receptor 1, and a protease that can degrade NTS.

In an embodiment of the present invention, the inhibitor of the neurotensin activation of the neurotensin receptor 1 is an agent down-regulating the expression of neurotensin or of neurotensin receptor 1 in lung cells. Typically, agent down-regulating the expression of neurotensin or of neurotensin receptor 1 comprises a nucleic acid which interferes with the expression of neurotensin or of neurotensin receptor 1.

Typically, the down-regulation of the NTS or NTRS1 expression may be measured by immunohistochemistry, binding assay, mRNA level for NTSR1 and radio-immunoassay or Enzyme link immunosorbent assay for NTS (Holtom P E, et al J Neurosci Methods. 100(1-2):151-6, 2000; Davis L G et al, J Neurosci Methods 15-23, 1985; Vincent J P Ann N Y Acad. Sci., 668:90-100, 1992; Souazé F et al., J Biol Chem, 272(15):10087-94, 1997).

Examples of such agents are antisense molecules or vectors comprising said antisense molecules. Antisense molecules are complementary strands of small segments of mRNA. Methods for designing effective antisense molecules being well known (see for example U.S. Pat. No. 6,165,990), it falls within the ability of the skilled artisan to design antisense molecules able to downregulate the expression of neurotensin or of neurotensin receptor 1 in lung cells. Further examples are RNA interference (RNAi) molecules such as, for example, short interfering RNAs (siRNAs) and short hairpin RNAs (shRNAs). RNAi refers to the introduction of homologous double stranded RNA to specifically target a gene's product, in the present case neurotensin or of neurotensin receptor, resulting in a null or hypomorphic phenotype. Methods for designing effective RNAi molecules being well known (see for review Hannon and Rossi Nature. 2004 Sep. 16; 431(7006):371-8), it falls within the ability of the skilled artisan to design RNAi molecules able to downregulate the expression of neurotensin or of neurotensin receptor in lung cells.

Examples of siRNAs able to downregulate the expression of neurotensin or of neurotensin regulator in lung cells are nucleic acid molecules which comprise one of the following sequences:

```
siRNA NTSR1:
5'-AAGAAGTTCATCAGCGCCATC-3'    (SEQ ID NO: 1)

siRNA NTS:
5'-GCAATGTTGACAATATACC-3'      (SEQ ID NO: 2)
```

In a further embodiment of the invention, the inhibitor of the neurotensin activation of the neurotensin receptor 1 is an antibody against neurotensin or a fragment thereof which binds to neurotensin, an antibody against the neurotensin receptor 1 or a fragment thereof which binds to the neurotensin receptor 1.

The person skilled in the art will be aware of standard methods for production of such specific antibody or fragment thereof. For example, specific antibodies or fragment thereof may be generated by immunizing an animal with neurotensin or with NTSR1 and by selecting the antibodies which inhibit the neurotensin activation of the neurotensin receptor 1.

Typically the inhibition of the neurotensin activation of the neurotensin receptor 1 may be measured with biological assays estimating the second messenger level, or the oncogenic cellular effect, or the morphological changes of the cells (Skrzydelski D et al Mol. Pharmacol. 64(2):421-9 2003; Xu-van Opstal W Y et al, Microsc Res Tech. 28(5):440-7 1994; Souaze F et al. Can Res 66(12):6243-9 2006).

The person skilled in the art will be aware of standard methods for production of both polyclonal and monoclonal antibodies and fragments thereof which binds to NTS or to NTSR1. Antibody fragments, particularly Fab fragments and other fragments which retain epitope-binding capacity and specificity are also well known, as are chimeric antibodies, and "humanized" antibodies, in which structural (not determining specificity for antigen) regions of the antibody are replaced with analogous or similar regions from another species. Thus antibodies generated in mice can be "humanized" to reduce negative effects which may occur upon administration to human subjects. Chimeric antibodies are now accepted therapeutic modalities with several now on the market. The present invention therefore comprehends use of antibody specific for neurotensin or NTSR1 which include $F(ab')_2$, $F(ab)_2$, Fab, Fv and Fd antibody fragments, chimeric antibodies in which one or more regions have been replaced by homologous human or non-human portions. The person skilled in the art will also be aware that fragments such as for example ScFv fragments and divalent ScFv-type molecules can be prepared using recombinant methods.

In a further embodiment of the present invention, the inhibitor of the neurotensin activation of the neurotensin receptor 1 is an antagonist of the neurotensin receptor 1. Antagonists of the neurotensin receptor 1 are well known. SR48692SR14294A are commonly used inhibitors of NTSR1 (see for example Gully et al. 1993, Proc. Natl. Acad. Sci. 90, 65-69 and Gully et al. 1997, J. Pharmacol. Exp. Ther. 280, 802-812). WO96/32382, WO95/32218, U.S. Pat. No. 5,430,047, U.S. Pat. No. 5,668,279 and EP0699438, for example, disclose families of antagonists of the neurotensin receptor 1.

In a further embodiment of the invention, the inhibitor of the neurotensin activation of the neurotensin receptor 1 is a protease that can degrade NTS. Examples of proteases that can degrade NTS are mast Cell carboxypeptidase A, neurolysin or human skin chymase. The protease may be administered to the subject in need thereof in its proteineous form or by gene therapy, for example by using a vector which enables the expression of the protease in situ.

The expression of NTSR1 by non-small cell lung cancer cells enables the specific targeting of non-small cell lung cancer cells with cytotoxic agent which binds to the neurotensin receptor 1.

The present invention provides a method for treating non-small cell lung cancer, comprising the step of administering an effective amount of a cytotoxic agent which binds to the neurotensin receptor 1 to a subject in need thereof.

Also provided is a cytotoxic agent which binds to the neurotensin receptor 1 for the treatment of non-small cell lung cancer. The cytotoxic agent which binds to the neurotensin receptor 1 may also be an antimetabolite.

Examples of cytotoxic agents which bind to the neurotensin receptor 1 may be selected from the group consisting of an antibody against the neurotensin receptor 1 or a fragment thereof which binds to the neurotensin receptor 1, neurotensin or a neurotensin analogue conjugated with a cytotoxic drug, and neurotensin or a neurotensin analogue labelled with a cytotoxic radioisotope.

Typically said antibody against the neurotensin receptor 1 or said fragment thereof which binds to the neurotensin receptor 1, may be conjugated with a cytotoxic drug or labelled with a cytotoxic radioisotope.

Alternatively, said antibody against the neurotensin receptor 1 or said fragment thereof which binds to the neurotensin receptor may trigger antigen-dependent cell-mediated cytotoxicity (ADCC) and/or complement dependent cytotoxicity (CDC). This may be achieved by introducing one or more amino acid substitutions in an Fc region of the antibody. Alternatively or additionally, cysteine residue(s) may be introduced in the Fc region, thereby allowing inter-chain disulfide bond formation in this region. The homodimeric antibody thus generated may have improved internalization capability and/or increased complement-mediated cell killing and/or antibody-dependent cellular cytotoxicity (ADCC) (Caron P C. et al. J Exp Med. 1992 Oct. 1; 176(4):1191-5 and Shopes B. J. Immunol. 1992 May 1; 148(9):2918-22.).

Neurotensin analogues are well known, WO98/33531, WO00/78796, WO2007/093373, U.S. Pat. No. 6,312,661 and U.S. Pat. No. 5,760,188, for example, provide families of neurotensin analogues. The neurotensin analogue may be an antagonist or an agonist of NTSR1.

Examples of cytotoxic drugs are platinum salts, taxanes, vinca derivatives and analogues, gemcitabine, methotrexate, doxorubicin, cytotoxin such as *Pseudomonas* exotoxin, g protein, and g protein coupled receptor inhibitors.

Common cytotoxic radioisotopes are, for example, $^{131}$I, $^{90}$Y, $^{77}$Lu, $^{67}$Cu, $^{186}$Re, $^{188}$Re, $^{212}$Bi and $^{213}$Bi.

In the context of the invention, the term "treating" or "treatment", as used herein, means reversing, alleviating, inhibiting the progress of, or preventing the disorder or condition to which such term applies, or reversing, alleviating, inhibiting the progress of, or preventing one or more symptoms of non-small cell lung cancer.

By a "therapeutically effective amount" of an inhibitor of the neurotensin activation of the neurotensin receptor 1 or of a cytotoxic agent which binds to the neurotensin receptor 1 is meant a sufficient amount to treat non-small cell lung cancer, at a reasonable benefit/risk ratio applicable to any medical treatment. It will be understood, however, that the total daily usage of the inhibitor or of the cytotoxic agent will be decided by the attending physician within the scope of sound medical judgment. The specific therapeutically effective dose level for any particular subject in need thereof will depend upon a variety of factors including the stage of non-small cell lung cancer being treated and the activity of the specific inhibitor/cytotoxic agent employed, the age, body weight, general health, sex and diet of the subject, the time of administration, route of administration, the duration of the treatment; drugs used in combination or coincidental with the and like factors well known in the medical arts. For example, it is well known within the skill of the art to start doses of the compound at levels lower than those required to achieve the desired therapeutic effect and to gradually increase the dosage until the desired effect is achieved.

Typically medicaments according to the invention comprise an inhibitor of the neurotensin activation of the neurotensin receptor 1 or a cytotoxic agent which binds to the neurotensin receptor 1, together with a pharmaceutically-acceptable carrier. A person skilled in the art will be aware of suitable carriers. Suitable formulations for administration by any desired route may be prepared by standard methods, for example by reference to well-known text such as Remington; The Science and Practice of Pharmacy.

A method of treatment according to the invention may be used in combination with any other therapeutic strategy for treating non-small cell lung cancer, e.g. surgery, external radiotherapy, chemotherapy or hormone therapy or cytokine therapy.

In a preferred embodiment, an inhibitor of the neurotensin activation of NTSR1 is used in combination with chemotherapy, i.e. in combination with an anti-cancer agent.

The expression of NTRS1 in non-small cell lung cancer cells is associated with a weak response to the chemotherapeutic agents, whereas the inhibition of the neurotensin activation of NTSR1 prompts the cell to respond to the chemotherapeutic agents.

As used herein, the expression "anti-cancer agent" or "chemotherapeutic agent" refers to compounds which are used in the treatment of cancer.

Anti-cancer agents include but are not limited to an antimetabolite such as pemetrexed, fludarabine, gemcitabine, capecitabine, methotrexate, taxol, taxotere, mercaptopurine, thioguanine, hydroxyurea, cytarabine, cyclophosphamide, ifosfamide, nitrosoureas, platinum complexes such as cisplatin, carboplatin and oxaliplatin, mitomycin, dacarbazine, procarbizine, etoposide, teniposide, campathecins, bleomycin, doxorubicin, idarubicin, daunorubicin, dactinomycin, plicamycin, mitoxantrone, L-asparaginase, doxorubicin, epimbicm, 5-fluorouracil, taxanes such as docetaxel and paclitaxel, leucovorin, levamisole, irinotecan, estramustine, etoposide, nitrogen mustards, BCNU, nitrosoureas such as carmustme and lomustine, vinca alkaloids such as vinblastine, vincristine and vinorelbine, imatimb mesylate, hexamethyhnelamine, topotecan, kinase inhibitors, phosphatase inhibitors, ATPase inhibitors, tyrphostins, protease inhibitors, inhibitors herbimycm A, genistein, erbstatin, and lavendustin.

In a preferred embodiment, the anti-cancer agent is selected from taxol; taxotere; platinum complexes such as cisplatin, carboplatin and oxaliplatin; doxorubicin; taxanes such as docetaxel and paclitaxel; vinca alkaloids such as vinblastine, vincristine and vinorelbine; genistein; erbstatin; an antimetabolite such as pemetrexed; and lavendustin.

Typically, before applying a method of treatment according to the present invention to a subject suffering from non-small cell lung cancer, a diagnostic test may be performed in order to determine whether the non-small cell lung cancer displays NTSR1-expressing cells. By performing such a pre-treatment diagnostic test, it is possible to determine whether a subject would be responsive to a method of treatment according to the invention.

It falls within the ability of the skilled artisan to carry out such a diagnostic test. Typically NTSR1 expression may be measured for example by RT-PCR or immunohistochemistry performed on a sample obtained by biopsy.

Alternatively, levels of neurotensin or a precursor thereof such as proneurotensin in a sample obtained from the subjects may be determined in order to treat only those subjects having an elevated level of neurotensin or a precursor thereof such as proneurotensin. Examples of samples obtained from the subjects are whole blood sample, plasma sample or serum sample. Neurotensin or proneurotensin survey may also be used to detect an eventual recurrence of the tumor and/or of metastases. Examples of method for measuring the levels of proneurotensin are given in WO2006/079528, in Ernst et al., Peptides 27 (2006) 1787-1793 and in Friry et al, Biochemical and Biophysical research Communication 290, 1161-1168 (2002).

In an embodiment of the invention, the subject in need thereof is a subject with stage I or II non-small cell lung cancer displaying NTSR1-expressing cells. The stages of lung cancer are defined for example in Clifton T. Mountain Chest 111; 1710-1717 1997.

The present invention also relates to a method of determining the prognosis of a subject suffering from non-small cell lung cancer, comprising the step of detecting the expression of NTSR1 in non-small cell lung cancer cells obtained from said subject, wherein the presence of expression of NTSR1 indicates that the subject has a poor prognosis.

In an embodiment of the invention, said subject is a subject with stage I or II non-small cell lung cancer.

The present invention thereby enables the evaluation of the risk of recurrence of a subject which has been surgically treated.

The term "detecting" as used above includes qualitative and/or quantitative detection (measuring levels) with or without reference to a control. Typically NTSR1 expression may be measured for example by RT-PCR or immunohistochemistry performed on a sample obtained by biopsy.

A method of prognosis according to the invention may be used in combination with any other methods already used for the staging of non-small cell lung cancer (see for example Clifton T. Mountain Chest 1997; 111; 1710-1717).

The invention also provides a method for predicting the response to treatment with an anti-cancer agent in a subject suffering from non-small cell lung cancer, comprising the step of detecting the expression of NTRS1 in non-small cell lung cancer cells obtained from said subject.

The presence of NTSR1-expressing cells is indicative of poor response to anti-cancer agent treatment.

The present invention also provides a method of detecting and localizing non-small cell lung cancer cells and their metastases in the body of a subject, to which a quantity sufficient for imaging of a labelled agent which binds to NTSR1 has been previously administered, comprising the step of subjecting said body to imaging.

Examples of labelled agents which bind to NTSR1 may be selected from the group consisting of a labelled antibody against the neurotensin receptor 1 or a fragment thereof which binds to the neurotensin receptor 1, a labelled neurotensin or a labelled neurotensin analogue.

It falls within the ability of the skilled artisan to carry out such a imaging method. Typically the label may be a fluorophore, a radioactive isotope or a paramagnetic agent. Labelled neurotensin analogue and their uses for imaging are well known see for example WO98/33531, WO00/78796, WO2007/093373, U.S. Pat. No. 6,312,661 and U.S. Pat. No. 5,760,188.

In the following, the invention will be illustrated by means of the following examples as well as the figures.

FIGURE LEGENDS

FIG. 1: Neurotensin (NTS) and neurotensin-receptor 1 (NTSR1) expression in patients with primary lung adenocarcinomas. A) Example of immunohistochemistry for NTSR1 (left) and NTS (right); Top: positive labeling of patients with primary lung adenocarcinomas. Original magnification ×100, ×200 (first line), ×400 (second line), Bottom: negative labeling of idiopathic pneumothorax ×200. For all cases, slides were obtained in paraffin wax embedded tissues. Immunohistochemistry for NTS and NTSR1 was performed according to a standard technique including a 60 min incubation with the primary antibody followed by incubation with a streptavidin-biotin-peroxidase complex. B) Percentage of patients positive for NTSR1 or NTS or both. Positivity was evaluated by an anatomopathologist. C) NTS and NTSR1 transcript analysis on RNA from patients with primary lung adenocarcinomas stage I. PCR was performed on a 1/5 dilution of a RT reaction containing 1 μg RNA, for 28 cycles Patients with red dot or green dot were considered has positive for NTS or NTSR1 respectively.

FIG. 3: Characterization of lung carcinoma cell lines, LNM35 and the derived clones, LNM-R and LNM-F. A) Typical morphological characteristics observed without (top lane) or with (bottom lane) phase contrast microscopy at the magnification 200×. B) Immunocytochemistry labeling for Vinculin (Top), Actin (middle), and DAPI staining (bottom) of LNM-R (left column) and LNM-F (Right column) C) RT-PCR analysis on 200 ng of LNM35, LMN-R and LNM-F total ARN. D) NTS radioimmunoassay performed on cellular media of 106 LMN-R or LNM-F cells grown for 24, 48 and 72 h. Experiments were performed 3 to 5 time in duplicates. E) Typical immunocytochemistry labeling for NTSR1 of LNM-R and LNM-F cells. Cells were seeded on sonic Seal slide grow for 48 h, immunocytochemistry was performed as described in the materiel and methods

FIG. 5: Silencing cell lines for NTS or NTSR1 (R-SI NTS and R-SI NTSR1, respectively) were generated from the LNM-R cell line. A) One μg of total RNA from LNM35, LNM-R, LNM-F, R-SI NTSR1, and R-SI NTS were reverse-transcribed. PCR experiments were performed using specific primers for NTS (top), and NTSR1 (bottom). Amplicons were electrophoresed on agarose gels and stained with ethidium bromide. B) NTS radioimmunoassay performed on cellular media of 106 LMN-R, R-SI NTSR1 or R-SI NTS cells grown for 24, 48 and 72 h. Experiment was performed 3 to 5 time in duplicates. C) One million cells from LNM-R, R-SI NTS, R-SI NTSR1, or a 50/50 mixture of R-SI NTS and R-SI NTSR1 were injected into 36, 21, 21, and 19 mice, respectively. Tumor volumes were measured every week. Ellipsoid formula (4/3 PI×(L/2×1/2×h/2) was used to calculate the volume. D) Tumor weight at 28 days. Significant differences at $***P<0.001$ using analysis of variance and Student-Neuman-Keuls test. E) Typical immunohistochemistry for NTSR1 (left) or NTS (right) for tumors generated from R-SI NTS (top) or R-SI NTSR1 cells (bottom). F) NTS and NTSR1 transcript analysis on tumors from LNM 35 R-SI NTSR1, LNM-F, LMN-R and R-SI NTS cells. Analysis was performed at day 28. Examples of two different tumors are shown.

FIG. 6: NTS endocrine regulation and enhancement of tumor growth. A) One million R-SI NTS cells were injected into the right mice flanks, and one million R-SI NTSR1 cells were injected into the left mice flanks of the same mouse (n=18). In a second set, one million LNM-R cells were injected only into the right mice flanks (n=36). Tumor volumes were measured every week. The ellipsoid formula (4/3PI×(L/2×1/2×h/2) was used to calculate the volume. B) Tumor weight at day 28, C) One million LNM35 or a 50/50 mixture of R-SI NTS and LNM-R cells or a 50/50 mixture of R-SI NTS and LNM-F cells were injected in the right mice flanks, 28, 17 and 14 mice were injected, respectively. Tumor volumes were measured every week. The ellipsoid formula (4/3 PI×(L/2×1/2×h/2) was used to calculate the volume. D) Tumor weight at day 28. Significant differences at *P<0.001 and p<0.01 using analysis of variance and Student-Neuman-Keuls test.

FIG. 7: A hypothetical mechanism for tumor growth enhancement by the NTS system. Autocrine, paracrine, and endocrine regulation may occur in an isolated or combined fashion. Autocrine or endocrine NTS regulation is associated with low tumor growth which is strongly enhanced the addition of a paracrine NTS regulation. NTS is known to potentiate cellular proliferation through several mechanisms, including EFG-like and IL8 release. One possible explanation for the boosting of tumor growth by NTS and the cooperation between cells with an autocrine NTS regulation and cells with paracrine regulation would be the increase of EGF-like ligands release at the neighboring of cells, causing a stronger activation of EGFRs, known for their major role in cell proliferation. The lack of NTSR1 expression at the cell surface results in very low tumor growth, indicating the participation of circulating and local NT in tumor progression.

EXAMPLES

In the following description, all molecular biology experiments for which no detailed protocol is given are performed according to standard protocol.

Example 1

Summary

We retrospectively evaluated the association of Neurotensin receptor 1 (NTSR1), or neurotensin (NTS), or both and survival among 71 patients with stage I primary lung adenocarcinoma. Experimental tumors were developed using an aggressive lung cancer cell line, expressing NTSR1, or NTS and NTSR1, or silenced for both.

Results: The expression of NTS and NTSR1 was found in (66%), and (59%) of the cases, respectively. Expression of both occurred in (43.6%) of patients. Expression of NTS has no impact on survival. Positive labeling of NTSR1 was associated with a significantly worse prognosis than negative labeling (5-year survival rate of 51.7% versus 90.2%; p=0.00027). Tumor size from cell lines expressing either NTS and NTSR1, or NTSR1 alone are 32% and 51% smaller, respectively, than from the mixture of the two cell lines. Depletion of NTS or NTSR1 in the cell line originally expressing both is accompanied by 35 and 60% decrease in tumor size, respectively.

Conclusion: NTS/NTSR1 complex enhance the lung tumor growth. The assessment of NTSR1 expression in low-stage tumors is a marker to discriminate between tumor aggressiveness.

Methods

Patients and Tissue Specimens

Clinical files of seventy-one consecutive patients treated by lobectomy and full nodal dissection for a pathologic stage I primary lung adenocarcinoma were retrospectively reviewed. All were operated on at the Thoracic Surgery Department of Hôtel-Dieu Hospital, Paris, France, between Jan. 8, 2001 and Mar. 27, 2003. All the patients had macroscopically and microscopically complete resection. None had pre-operative or postoperative chemotherapy or radiotherapy. For all cases histologic slides of primary tumor were obtained by paraffin wax embedded tissues. Standard H&E staining was used to ensure the tumoral character of the specimen and adjacent sections were obtained for immunohistochemistry.

Immunohistochemistry

Immunostaining of NTSR1 and NTS was carried out on deparaffinized sections of 4 μm thick, using the avidin biotin peroxidase complex method. After inhibition of endogenous peroxidases with 3% hydrogen peroxide, slides were washed in TBS and incubated with 10% normal rabbit serum at room temperature (RT) for 30 min. NTSR1 immunoreactivity was detected using a goat polyclonal antibody directed against the human carboxy terminus of the receptor (1:100) (C-20 Santa Cruz USA). NTS immunoreactivity was conducted using rabbit antibody directed against NTS (1/500) (NA1230 Biomol, USA) for 2 hours at RT in a humidified chamber for human tumor and with NTS long fragment, FL170 (Santa Cruz) at the dilution 1/200 for xenografted tumors. NTS or NTSR1 immunohistochemistry specificity was checked by omission of primary antibody and displacement with neutralizing peptide (Santa Cruz, USA) or NTS, for 2 hours at RT. All slides were rinsed tree times with TBS; sections were incubated with biotinylated secondary antibody (1:200) (Vector, USA), for 30 min at RT. The antigen-antibody complex was revealed with avidin-biotin-peroxidase complex, for 30 min, according to the manufacturer's instructions for the Vectastain ABC Kit (Vector, USA). Staining was done for 5 min with diamino-benzidine tetrahydrochloride (DAB) (Sigma, USA). All slides were counterstained with hematoxylin. Same procedure was used for mice tumor.

Culture Procedure

The human lung adenocarcinoma cell lines, NCI-H460 and LNM35 was grown in RPMI-1640 medium (Invitrogen, USA) supplemented with 10% fetal calf serum and 2 mM glutamine. LNM35 cell line was sub-cloned by limiting dilution, after few days culture, clones containing exclusively flat or rounded cells were saved and were named LNM-F for Flat, LNM-R for Rounded.

RNA Extraction and RT-PCR

The protocols for total RNA extraction, reverse-transcription reaction (RT), and PCR are documented in Souaze et al. RT was performed on 2 μg of total RNA using a specific NTSR1 primer (5'-GCTGACGTAGAAGAG-3' SEQ ID NO:3) or 50 pmol of oligo dT and oligo dN. The PCR amplification was performed on a 1:5 v/v of the RT reaction using 25 pmol of each primer 5'-CGTGGAGCTGTACAACTTCA-3' SEQ ID NO:4 and 5'-CAGCCAGCAGACCACAAAGG-3' SEQ ID NO:5 for NTSR1, and 5'-CAGCTCCTGGAGTCT-GTGCT-3' SEQ ID NO:6 and 5'-GTTGAAAAGCCCTGCT-GTGACAGA-3' SEQ ID NO:7 for NTS, S: 5'-TTCAAAT-GAGATTGTGGAAAA-3' SEQ ID NO:8 and AS: AGATCATCTCTGCCTGAGTAT SEQ ID NO:9 for Cox-2, 5'-CGGAGTCAACGGATTTGGTCG-3' SEQ ID NO:10 and 5'-TTCACCACCATGGAGAAGGCT-3' SEQ ID NO:11 for GAPDH and 1 unit of Taq polymerase (Applied Biosystems, Courtaboeuf, France). The amplification profile consisted of denaturation at 94° C. for 30 s, annealing at 57° C. for 45 s, and extension at 72° C. for 45 s. The PCR cycles were preceded by denaturation at 95° C. for 5 min and were followed by a final extension at 72° C. for 10 min. Amplification was performed in a DNA thermal cycler 9700 (Perkin Elmer Applied Biosystems, Courtaboeuf, France).

NTSR1 and NTS SiRNA Construction and Transfection

Si-RNAS for human NTSR1 (5'-AAGAAGTTCAT-CAGCGCCATC-3' SEQ ID NO:1) and NTS (5'-GCAATGT-TGACAATATACC-3' SEQ ID NO:2) were prepared using psilencer 3.1-H1 according the manufacturer's instruction (Ambion, USA). LNM-R cells were transfected using Lipofectamine reagent (Invitrogen, USA). Stable transfectants were selected with hygromycin B (400 μg/ml) and colonies were screened using RT-PCR (Souaze F et al, Cancer Res 66(12):6243-9 2006).

Immunocytochemistry

LNM35, LNM-R and LNM-F were plated on 4 wells sonicSeal slide (Nunc). Briefly, cells were fixed 2 min by acetone/methanol (V/V) solution and NTSR1 receptor labelling was performed with polyclonal antibody (1/500) (c2206, sigma) and revealed with secondary FITC anti-rabbit antibody (1/200). Actin polymerization was detected by incubation of the slides for 30 min with TRITC-conjugated phalloidin (Sigma) in PBS-1% BSA. For vinculin immunostaining, the slides were incubated for 1 h with vinculin antibody (Sigma) 1/100 in PBS-0.5% BSA. Slides were subsequently incubated for 1 h with FITC goat anti-mouse IgG (Immunotech, Marseille, France). Slides were mounted using the Vectashield-diamidino-phenylindole medium (DAPI, Vector, Burlingame, Calif., USA).

NTS Radioimmunoassay

One million of cells were grown in 60 mm Petri dishes, after 24 h media was removed and serum free media was added the cells for 24, 48, or 72 h. Media was collected; centrifuged 5 min at 2000 g, 5000 UIK/ml of trasylol was added to media. Radio-immunoassay was performed on 1 ml of lyophilized media according the procedure developed in Scarceriaux et al (Scarceriaux V et al. Endocrinology; 136 (6):2554-60, 1995). Briefly, serial dilution of NTS (Sigma) or unknown samples were incubated in 1 ml final assay buffer (60 mM $NaH_2PO_4$, 10 mM EDTA, pH 7.4) with the anti-NTS antibody (final dilution 1/33 300) A44 (Euro Diagnostica), and [$^{125}$Ityr]-NTS 5000 dpm; 2000 Ci/mmol at 4° C. for 5 days. Bound [$^{125}$Ityr]-NTS was separated from free radioligand by precipitation with 16% Polyethylene glycol and 5 mg/ml rabbit gamma-globulin. After centrifugation (2,500×g for 20 min), the radioactivity remaining in the pellet was measured in a gamma-counter (Wallac model 1470 Wizard).

Animals

Xenografts were initiated by subcutaneous injection of LNM35, or LNM-F, LNN-R or R-SI NTS or R-SI NTSR1. Cells were defrosted from $N_2$ liquid; grown in appropriate media, splitted 2 to 5 times before being plated at the concentration of $10^6$ cells in a T75 flask. After 72 h, cells were trypsinized, counted twice using Neubauer counting cells, and resuspended in PBS at the concentration of $10^6$ cells/100 μl. 100 μL were injected per animals. A minimum of 6 animals per group was used. For tumor generate from cell mixture, cells were plated together in T150 flask at $10^6$ cells of each clones (LNM-R and LNM-F, or R-SI NTS and R SI NTSR1). Cell mixtures were grown for 72 h before trypsinization. 100 μl of PBS containing $10^6$ cells were injected per animal. One group of animal was injected in the right flank with $10^6$ of R-SI NTS and in the left flank with 106 R-SI NTSR1 cells. The tumor volume was calculated using the ellipsoid formula ((4/3×PI×(length/2)×(width/2×(High/2)). Mice were sacrificed after 28 days, tumors were dissected and weighed. Portion of the tumor was immediately frozen in $N_2$ liquid and a portion was fixed in 4% Paraformaldehyd. Paraffin block were made and XX μn slices were made.

Statistical Analysis

One-way Analysis of Variance (ANOVA) followed by Student-Newman-Keuls Multiple Comparisons Test was used to determine the variation between the volume and the weight among tumors from diverse cell lines origin. Survival was calculated by Kaplan-Meyer method and comparison of survival curves was performed by the log-rank test.

Results:

Expression of NTS and NTSR1 in Human Lung Adenocarcinomas

Expression of NTS and NTSR1 were studied by immunohistochemistry in a series of 71 consecutive patients undergoing pulmonary lobectomy and nodal dissection for pathological stage I lung adenocarcinomas. The patient clinical characteristics are shown in table 1.

TABLE 1

Patient clinical characteristics. Seventy-one consecutive patients treated by lobectomy for pathological stage I primary lung adenocarcinoma were studied. None had undergone peri-operative chemotherapy or radiotherapy.

| Lung adenocarcinomas n = 71 | |
| --- | --- |
| Age | 59.6 ± 10.7 |
| Men | 59/71 |
| T1 | 28/71 |
| T2 diseases | 43/71 |
| Tumor size (cm) [mean ± SD] | 3.8 ± 2.07 |
| N0 | 71/71 |
| Intratumoral or peri-tumoral neoplastic vascular emboli | 24/71 |
| Intratumoral or peri-tumoral neoplastic lymphatic emboli | 15/71 |
| NTSR1 positive tumors [n (% of patient)] | 45/71 (63%) |
| NTS positive tumors [n (% of patient)] | 46/71 (65%) |
| NTSR1 and NTS positive tumors [n (% of patient)] | 31/71 (44%) |
| Lost at follow-up | 1/71 |
| Follow-up in months [mean ± SD] | 48.2 ± 20.9 |
| Deaths during follow-up [n (% of patient)] | 22/70 (31%) |
| Pen-operative therapies | |
| Radiotherapy [n] | 0/71 |
| Chemotherapy [n] | 0/71 |
| Idiopathic pneumothorax n = 26 | |
| NTSR1 positive lung parenchyma | 0/26 |
| NTS positive lung parenchyma | 0/26 |
| NTSR1 and NTS positive lung parenchyma | 0/26 | n = number of patient,
SD = standard deviation

Figure 1:
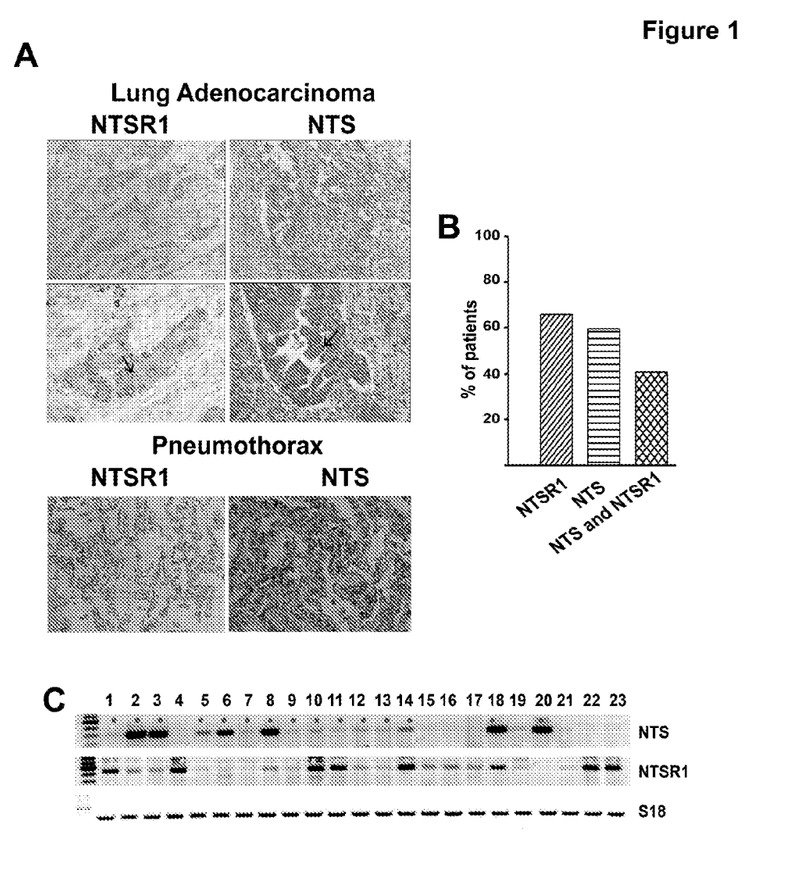
Figure 2:
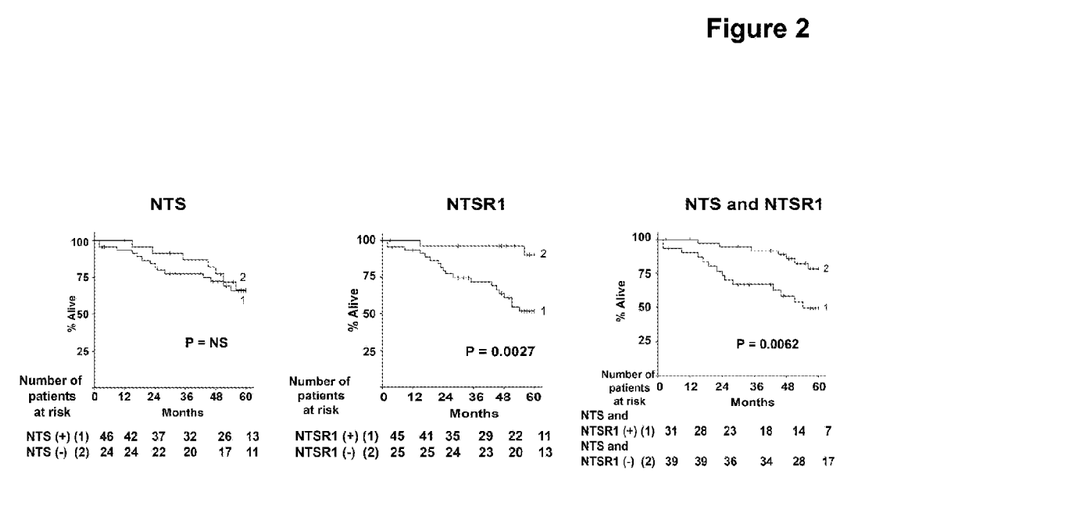
FIG. 2: Survival curves are shown with respect to the expression (1) or not (2) of NTS (right), NTSR1 (middle), or of the NTS/NTSR1 complex (Left). Survival analysis was performed according to the Kaplan-Meyer method and comparison made by the log-rank test. The number of patients at risk for each time period is shown below each curve.

NTSR1 staining in cancer cells was granular with the staining mainly restricted to the cytoplasm, and rarely at the cell surface, as shown FIG. 1A left. The labeling of the NTS was often very intense and always distributed in the entire the cytosol. For the most part, all cancer cells were labeled with NTS, whereas the tumor stroma was negative. A typical image of the observed NTS immunostaining is shown in FIG. 1A right. All specimens were scored by an anatomopathologist. The expression of NTS and NTSR1 was found in 46/71 (66%), and 45/71 (59%) of the cases, respectively. Expression of NTS and NTSR1 occurred in 31/71 (43.6%) of patients (FIG. 1B). Similar result were found when NTS and NTSR1 transcripts were studied, 15/23 (65%) patients expressed NTS (red dots on FIG. 1C) and 16/23 (69%) expressed NTSR1 (green dots on FIG. 1C). Ten patients out of 23 (43%) expressed both markers Expression of NTS as assessed by immunohistochemistry has no impact on survival (FIG. 2, left), whereas expression of NTSR1 was associated with a significantly worse prognosis than absence of NTSR1 expression (5-year survival rate of 51.7% versus 90.2%; p=0.00027) (FIG. 2 middle). Patient with tumors expressing both markers had also a significantly worse prognosis that those with tumors expressing only NTS or only NTSR1 or none of them (5-year survival rate of 49.5% versus 78.5%; p=0.018, FIG. 2 right).

This result raises the question, if NTSR1 expression, in patient with a worse outcome, is only a prognosis marker because its expression would be correlated with other molecular events associated with tumor progression or if NTSR1 is also an actor and participates to enhance tumor progression. To answer this question we used experimental tumor.

Characterization of Cellular Models

Figure 3:
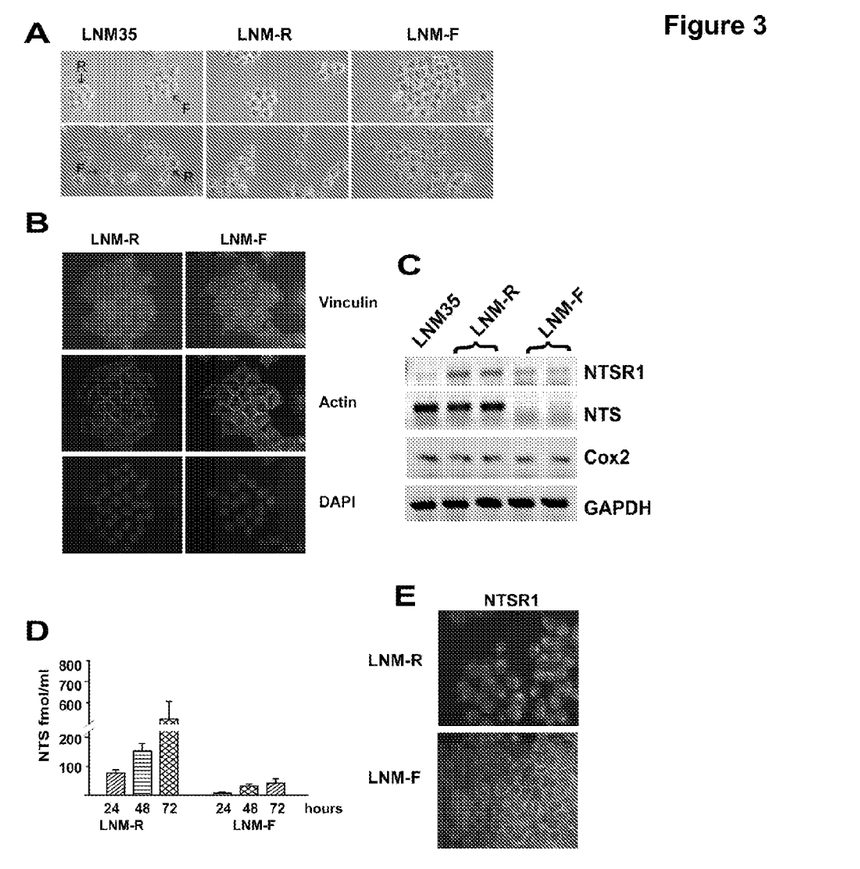

LNM35 cells originally derived from a human large cell carcinoma of the lung, the NCI-H460 cells. LNM35 has been shown to metastasize to regional lymph nodes with a 100% incidence as a result of conventional subcutaneous implantation. Microscopic observation of LNM35 cell line reveals two different morphological subpopulations of cells (FIG. 3A, high panel). One population is characterized by a convex and rounded appearance, named LNM-R, (FIG. 3A, middle). The other population is flattened, and more spread out, LNM-F. Each population was sub-cloned by limiting dilution. In agreement with the morphological discrepancy of the two sub-clones, immunocytochemistry of vinculin and actin reveals distinct protein profiles. In LNM-R cells, actin and vinculin labeling was decreased compared to the LNM-F cells (FIG. 3B). In LNM-F cells, vinculin labeling was concentrated in foci, which are known to augment adhesion and spreading by promoting recruitment of cytoskeletal proteins to the focal adhesion complex. In the same way, actin labeling confirmed the dissimilarity in cell spreading and showed an apparent size difference within the two sub-clones. Transcript analysis demonstrated that both sub-clones express NTSR1, but only LNM-R expressed NTS (FIG. 3C). We confirmed the differential expression of NTS in the two sub-clones by RIA. The culture media of LNM-R cells contained large amounts of NTS which accumulated with time, whereas the media from the LNM-F cells contained 20 times less NTS (FIG. 3D). NTS immunocytochemistry examination of both cell subtypes remained negative suggesting that the majority of NTS was released in the media (data not shown). Autocrine regulation was confirmed in LNM-R cells with a NTSR1 immunocytochemistry experiment (FIG. 3E). In LNM-F cells, NTSR1 is localized at the cell surface, demonstrating the naive status of the cells. In contrast, in LNM-R cells, NTSR1 is located in a peri-nuclear area, suggesting an intense internalization of the receptor. In order to confirm that both cell types were from the same origin, microsatellite analysis using D17S250 and D17S513, and showed identical patterns for LNM-R, LNM-F and LNM35, confirming the derivation of each two clones from LNM35.

NTS-NTSR1 Complex Enhance Tumor Growth

Figure 4:
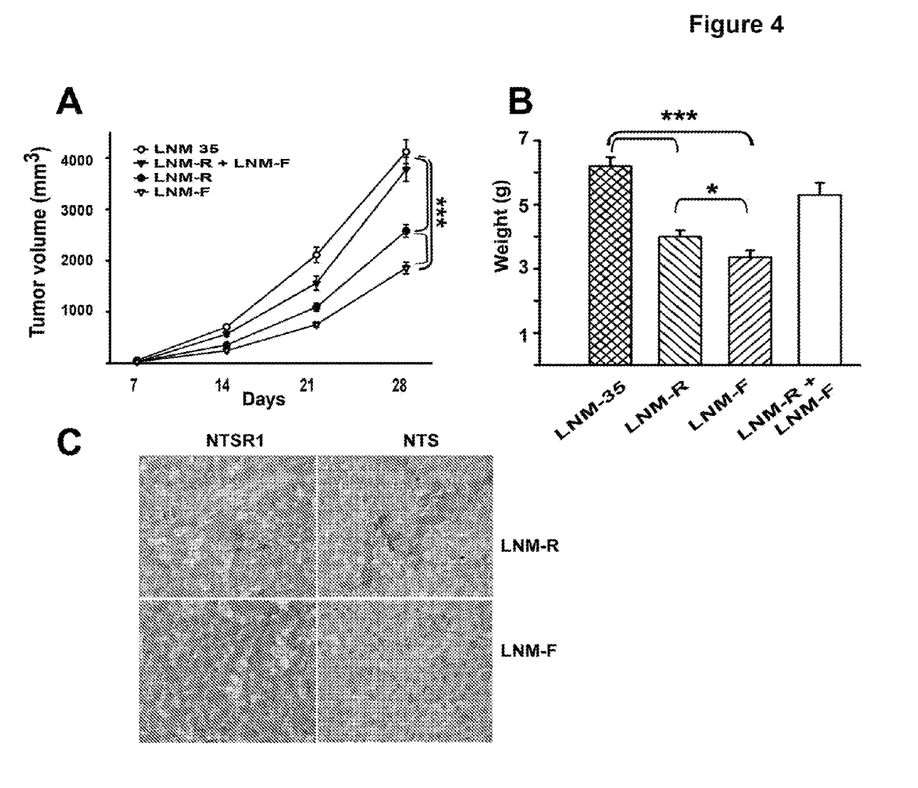
FIG. 4: Tumor growth generated by LNM35, LNM-R and LMN-F cells xenografted into nude mice. A). One million cells from LNM35, LNM-R, LNM-F, or a mixture of LNM-R and LNM-F (50/50) were subcutaneously injected in 24, 36, 34, or 12 nude mice, respectively Tumor volumes were measured every week. Ellipsoid formula (4/3 PI×(L/2×1/2×h/2) was used to calculate the volume. B) Tumor weight at 28 days. C) Typical immunohistochemistry for NTSR1 (left) or NTS (right) for tumors generated from LNM-R (top) or LNM-F (bottom) cells. Significant differences at $*P<0.001$ or $P<0.01$ using analysis of variance and Student-Neuman-Keuls test.

We first compared the rate of tumor growth of LNM35 and the two derived sub-clones, LNM-R(NTS+) and LNM-F (NTS−). As shown in figure. 3A, LNM35 displayed the more drastic tumorigenesis profile with a final tumor volume of 3802 mm$^3$. The sub-clones LNM-R, and LNM-F generated smaller tumors with a final volume of 2582 and 1858 mm$^3$, respectively. The tumor size is 32% and 51% smaller than LNM35 when generated by LNM-R or LMN-F, respectively. The difference in the tumor growth rate between the parental cells and the two sub-clones suggested cooperation between the two cellular populations which enhance the cell tumor potential. To confirm this hypothesis, we mixed the two sub-clones at equal concentration in the culture flask before injecting the mixture into the mice. The same rate of tumor growth than that of generated by LNM35 cells was observed, with a final volume of 3782 mm$^3$ for the mixture of LNM-F and LNM-R and 3802 mm$^3$ for LMN35 (FIG. 4A). The tumor weight observed at 28 days after injection followed the same variation as the tumor volume (FIG. 3B). NTS and NTSR1 immunohistochemistry was performed on tumor. The presence of NTSR1 was seen in both LNM-R and LNM-F tumors (FIG. 4C), the labeling is granular with irregular intensity as observed in human tissue (Showed in FIG. 1A). In order to visualize NTS, we used an antibody against a NTS precursor. Only under this condition, NTS was detectable in LMN-R but not in LNM-F tumors (FIG. 4C).

Figure 5:
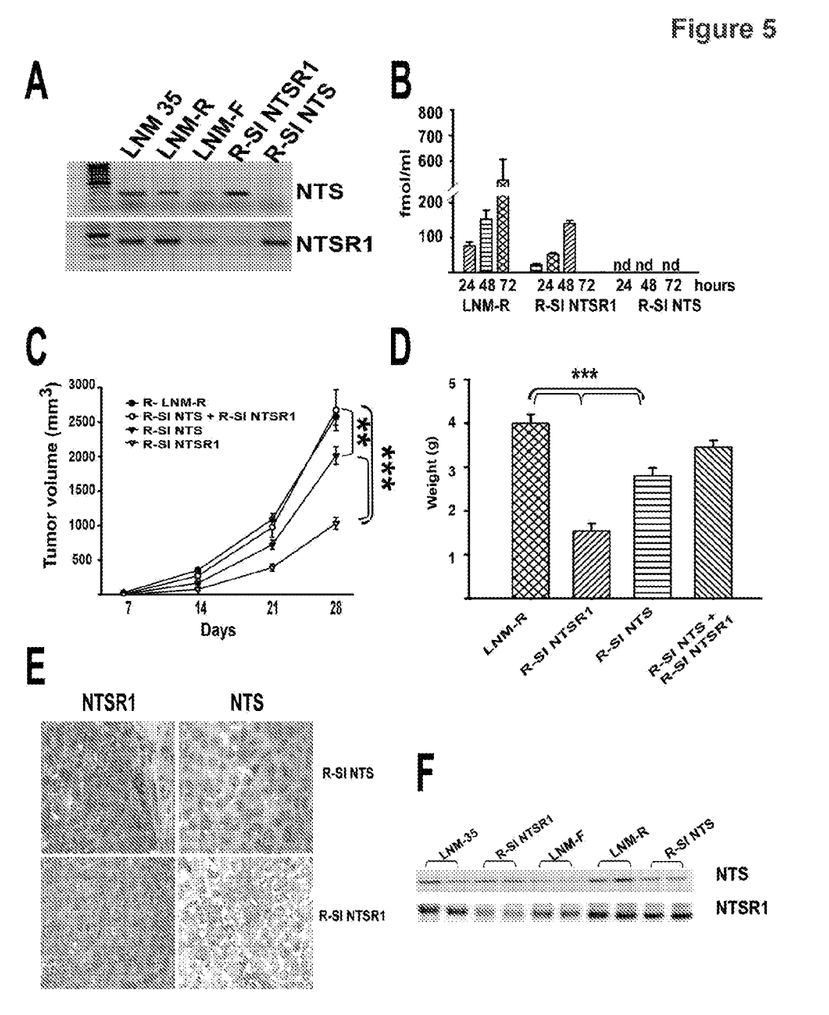

To evaluate the role NTS-NTSR1 complex in tumor growth enhancement, we generated silencing cell lines for NTS or NTSR1 from LMN-R cells. In the clone R-SI NTS, the transcript for NTS is completely depleted. We confirmed this result by NTS RIA performed on the cellular culture media, and as expected NTS was not detected (FIGS. 5A and B). Transcript analysis showed that in R-SI NTS, NTS-1 transcript is similar than in LNM35 and LNM-R cells. In the clone, R-SI NTSR1, the transcript for NTSR1 is mostly depleted, whereas the NTS transcript is similar to those found in LNM35 and LMN-R cells (An example is shown in FIG. 5A).

Using these cellular models, we examined the effect of NTS or NTSR1 depletion on the tumor growth of LNM-R cells and its NTS and NTSR1 silencing counterpart. Depletion of NTS or NTSR1 in the cells is accompanied by respectively 35 and 60% decrease of the tumor volume compared to the LNM-R tumor (FIG. 5C). A similar decrease was observed in tumor weight (FIG. 5D). A mixture of the two silenced clones, at equal concentration, was cultured for 3 days, prior injection into mice The final tumor volume and weight were similar than LNM-R tumor volume (FIGS. 5C and D). This observation suggest that a cooperation between the two cells lines R-SI NTS and R-SI NTSR1 occurred and boost the tumor growth (FIG. 5C), and NTS paracrine regulation is one of a major actor of this cooperation. We verified that the NTS and NTSR1 transgenes were still efficient after 28 days of tumor growth; By immunohistochemistry NTS and NTSR1 labeling were not detectable in R-SI NTS and R-SI NTSR1 respectively (FIG. 5E). Nevertheless, transcript analysis shows a higher expression of NTS and NTSR1 in the tumor RNA than in the original cell line (compare FIGS. 5F and 5A).

Figure 6:
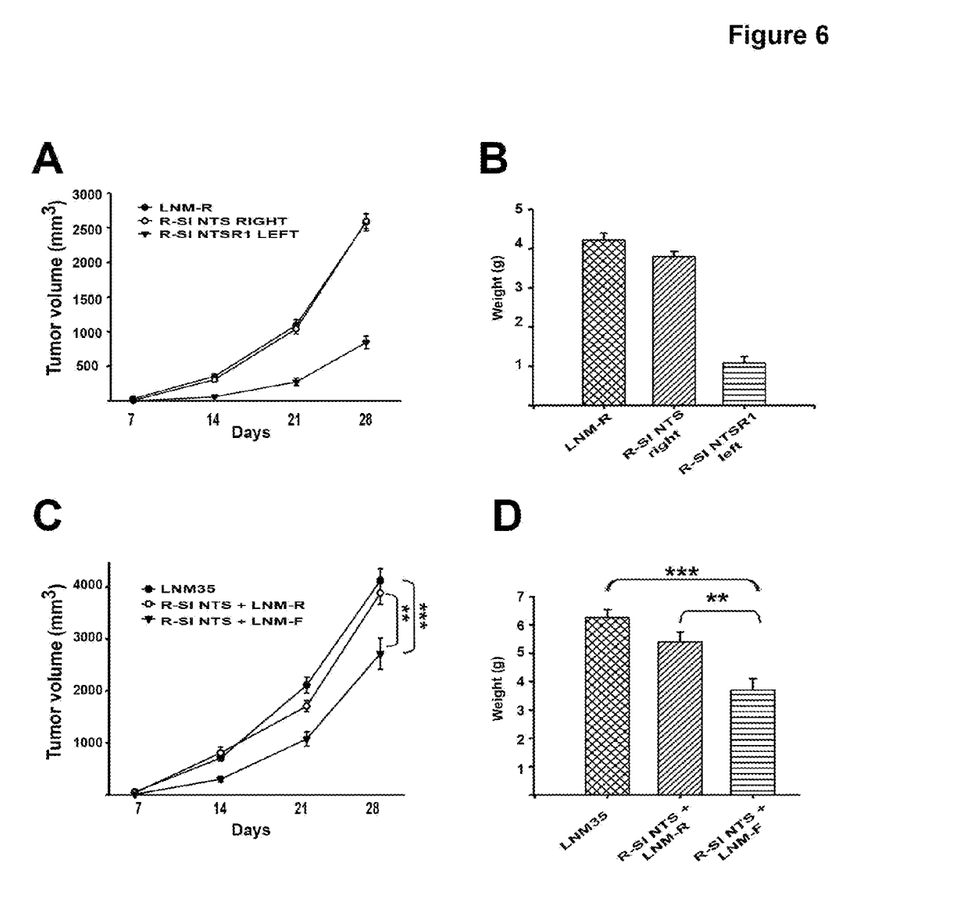
Figure 7:
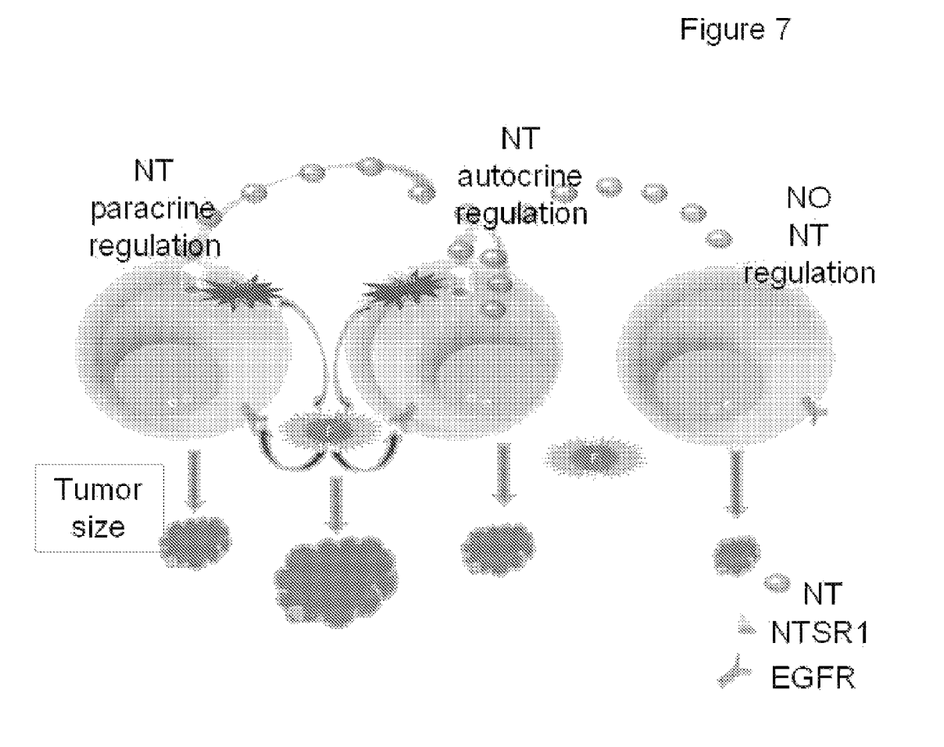

In order to explore the effect of NTS endocrine regulation on the tumor growth enhancement, R-SI NTS cells were injected in the right flank and R-SI NTSR1 cells in the left flank of the mice. The FIG. 6 shows that the R-SI NTS cells reach the size and the weight of the parental cells, LMN-R, whereas the R-SI NTSR1 tumor remains at the same small size that was observed in mice bearing the R-SI NTSR1 alone (compare FIG. 6 and FIG. 5C). We suggest that the circulating NTS produced by the SI-NTSR1 tumor enhanced the tumor growth of R-SI NTS xenografted into the other flank. Unfortunately, the amount of blood that can be obtained from nude mice is too small to perform a NTS RIA. The cooperation between the two cells line to enhance tumor growth is mediated by endocrine factors. This experiment suggested that NTS controls the cooperation and tumor growth enhancement.

We next addressed the question of the potency of the NTS autocrine regulation compared to the paracrine regulation. A mixture of R-SI-NTS and LNM-R cells at equal concentration were injected to mice. This mixture displayed NTS autocrine and paracrine regulation. After 28 days of growth, the size of the tumor generate by this mixture was similar to tumors generated by the parental LNM35 cells, 4122 mm$^3$ compared to 3885 mm3, respectively. At 28 days the tumor weight of LNM35 and the mixture of R-SI-NTS and LNM-R is similar (FIG. 6D), demonstrating that the NTS autocrine regulation generated cellular events which participate with paracrine regulation to strongly enhance tumor progression. In contrast, when a mixture of cells not expressing NTS, R-SI NTS and LNM-F, were injected the tumor volume and the tumor weight were 39% and 45%, respectively smaller than the LNM 35 cells. The tumor size and weight were similar to those of R-SI NTS or LNM-F when they were injected alone (1970, 1858 mm$^3$, respectively) compared to 2493 mm$^3$ for the mixture. Identical observations were made for the tumor weight. When the cells do not secrete NTS, there is no cooperation between cells, and tumor growth remains small. The overall experiment suggested that NTS participates in enhancing tumor growth and consequently to tumor progression gravity.

Example 2

Figure 8:
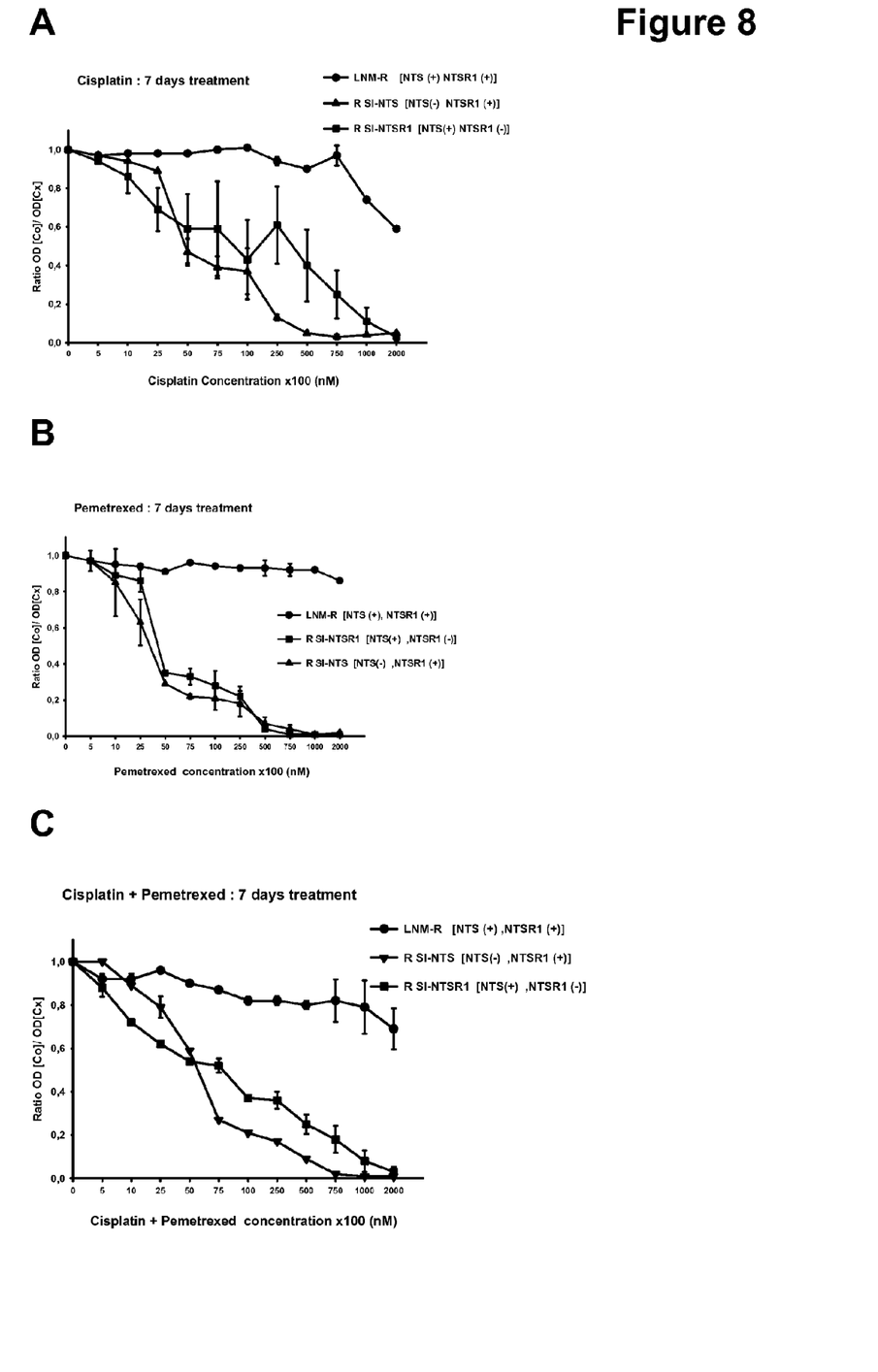
FIG. 8: 5000 cells were seeded in 24 wells dishes and treated with increased concentrations of Cisplatin (A), Pemetrexed (B), or both (C). MTT viability test are performed after 7 days of treatment. The results are expressed as the ratio of the OD of non treated cells to the OD of treated cells at their respective drug concentration. (Mean±SD)

Expression of NT-NTRS1 in Lung Cancer Cells is Correlated with Chemotherapy Resistance LNM R cells form a cellular subpopulation from the very aggressive cell line LNM35. This cells line exhibits NTS and NTSR1 expression. NTSR1 immunohistochemistry of LNM R cells show an accumulation of the receptor in the cytosol and in the perinuclear compartment, indicating the endocytosis of NTSR1 upon NTS stimulation. Silenced cell lines for NTS (R SI-NTS) or NTSR1 (R SI-NTSR1) were generated from LNM R. In the following experiment we studied the response of the cells and the silenced clones to the chemotherapy treatment currently proposed for the advanced lung cancer patients. 5000 cells were seeded in 24 wells dishes and treated with increased concentrations of Cisplatin (FIG. 8A), Pemetrexed (FIG. 8B), or both (FIG. 8C). MTT viability test are performed after 7 days of treatment. The results are expressed as the ratio of the OD of non treated cells to the OD of treated cells at their respective drug concentration.

In these experiments, NTS autocrine regulation was associated with a weak response to the chemotherapeutic agents even at very high concentration, whereas in the absence of NTS regulation the abolition of either NTS or NTSR1 expression prompts the cell to respond to the chemotherapeutic agents. The initial responses are observed at low concentrations (2.5 microM).

These results support the hypothesis that NTSR1 is an effective predictive marker for the response to chemotherapy treatments for patients with non-small cell lung cancer.

REFERENCES

Throughout this application, various references describe the state of the art to which this invention pertains. The disclosures of these references are hereby incorporated by reference into the present disclosure.

The invention claimed is:

1. A method for treating non-small cell lung cancer (NSCLC) comprising the step of administering an effective amount of an inhibitor of the neurotensin activation of neurotensin receptor 1 (NTSR1) to a subject in need thereof, wherein the inhibitor of the neurotensin activation of NTSR1 is selected from the group consisting of an antibody against neurotensin, and a fragment thereof which binds to neurotensin.

2. The method of claim 1, wherein the inhibitor is used in combination with an anti-cancer agent.

* * * * *